US010593082B2

(12) United States Patent
Crespo-Diaz et al.

(10) Patent No.: US 10,593,082 B2
(45) Date of Patent: Mar. 17, 2020

(54) DYNAMIC DISPLAY OF MULTI-PARAMETER QUANTITATIVE BIOLOGICAL DATA

(71) Applicant: Becton, Dickinson and Company, Franklin Lakes, NJ (US)

(72) Inventors: Oliver Crespo-Diaz, San Jose, CA (US); Alexander Fainshtein, San Jose, CA (US); Mengxiang Tang, San Jose, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 3 days.

(21) Appl. No.: 16/025,537

(22) Filed: Jul. 2, 2018

(65) Prior Publication Data

US 2019/0026927 A1    Jan. 24, 2019

Related U.S. Application Data

(60) Provisional application No. 62/608,241, filed on Dec. 20, 2017, provisional application No. 62/534,004, filed on Jul. 18, 2017.

(51) Int. Cl.
*G06T 11/00* (2006.01)
*G06T 11/20* (2006.01)
(Continued)

(52) U.S. Cl.
CPC ........ *G06T 11/206* (2013.01); *G01N 15/0227* (2013.01); *G01N 15/1429* (2013.01);
(Continued)

(58) Field of Classification Search
CPC combination set(s) only.
See application file for complete search history.

(56) References Cited

U.S. PATENT DOCUMENTS

| 4,845,653 A | 7/1989 | Conrad et al. |
| 5,627,040 A | 5/1997 | Bierre et al. |
| (Continued) | | |

FOREIGN PATENT DOCUMENTS

| FR | 2 935 802 | 3/2010 |
| WO | WO 2006/015056 | 2/2006 |
| (Continued) | | |

OTHER PUBLICATIONS

International Search Report for International Application No. PCT/US2018/040626 dated Sep. 13, 2018.
(Continued)

*Primary Examiner* — Wesner Sajous
(74) *Attorney, Agent, or Firm* — Bret E. Field; Bozicevic, Field and Francis LLP

(57) ABSTRACT

Data visualization features are described that provide a fast and accurate tool for displaying visualizations of high parameter data. The visualization features include graphically representing multiple parameters simultaneously with the associated statistical data for each parameter in an interactive way that maintains the contextual relationships between parameters and the related cell population. The visualization may be dynamically generated based on the measurements for the cell population and the resources available to the display device. The visualization features may be used for displaying high parameter multi-color flow cytometry or genomic data sets.

22 Claims, 5 Drawing Sheets

(51) Int. Cl.
*G06T 3/40* (2006.01)
*G06T 11/60* (2006.01)
*G06T 3/60* (2006.01)
*G06F 3/048* (2013.01)
*G01N 15/02* (2006.01)
*G01N 15/14* (2006.01)
*G06F 3/0484* (2013.01)
*G01N 15/10* (2006.01)

(52) U.S. Cl.
CPC ............ *G01N 15/1459* (2013.01); *G06T 3/40* (2013.01); *G06T 11/001* (2013.01); *G06T 11/60* (2013.01); *G01N 2015/1006* (2013.01); *G01N 2015/1477* (2013.01); *G06F 3/04842* (2013.01); *G06F 3/04847* (2013.01)

(56) References Cited

U.S. PATENT DOCUMENTS

| | | | |
|---|---|---|---|
| 5,739,000 | A | 4/1998 | Bierre et al. |
| 5,795,727 | A | 8/1998 | Bierre et al. |
| 5,962,238 | A | 10/1999 | Sizto et al. |
| 6,014,904 | A | 1/2000 | Lock |
| 6,944,338 | B2 | 9/2005 | Lock et al. |
| 8,990,047 | B2 | 3/2015 | Zhu et al. |
| 9,567,645 | B2 | 2/2017 | Fan et al. |
| 2012/0120520 | A1* | 5/2012 | Childress ............... B82Y 25/00 360/69 |
| 2012/0245889 | A1 | 9/2012 | Zhu et al. |
| 2013/0108139 | A1* | 5/2013 | Binnig ................. G06T 7/0012 382/133 |
| 2014/0275709 | A1* | 9/2014 | Khorrami ............ A61N 5/1031 600/1 |
| 2017/0132450 | A1* | 5/2017 | El-Zehiry .......... G01N 15/1463 |
| 2017/0268981 | A1 | 9/2017 | Diebold et al. |

FOREIGN PATENT DOCUMENTS

| | | |
|---|---|---|
| WO | WO 2013/054502 | 4/2013 |
| WO | WO 2016/094720 | 6/2016 |

OTHER PUBLICATIONS

International Search Report for International Application No. PCT/US2018/040621 dated Sep. 13, 2018.
Brunhart-Lupo et al. "Simulation exploration through immersive parallel planes." 2016 Workshop on Immersive Analytics (IA), IEEE, Mar. 20, 2016. pp. 19-24.
Falkman, Goran. "Information visualization in clinical Odontology: multidimensional analysis and interactive data exploration." Artificial Intelligence in Medicine. 22(2):133-158. May 1, 2001.
Johansson et al. "On the usability of three-dimensional display in parallel coordinates: Evaluating the efficiency of identifying two-dimensional relationships." Information Visualization. Jan. 1, 2014. pp. 29-41. London, England. Retrieved from the Internet: http://webstaff.itn.liu.se/~jimjo94/papers/Eval_3DPC_IVJournal.pdf.
Maksakov, Evgeny. "FlowCytoVis: Visualization Tool for Flow Cytometry Data Standards Project." Dec. 15, 2006. http://www.cs.ubc.ca/~tmm/courses/old533/projects.htm. Retrieved from the internet: http://www.cs.ubc.ca/~tmm/courses/old533/projects/evgeny/report.pdf. Retrieved on Sep. 4, 2018.
Rubel et al. "PointCloudXplore: Visual Analysis of 3D Gene Expression Data Using Physical Views and Parallel Coordinates." Eurovis-Eurographics / IEEE VGTC Symposium on Visualization, Jan. 1, 2006.
Streit et al. "3D parallel coordinate systems—A new data visualization method in the context of microscopy-based multicolor tissue cytometry." NIH Public Access Author Manuscript, vol. 69A, No. 7, May 5, 2006. pp. 601-611.
Bauer et al. (eds.), Clinical Flow Cytometry: Principles and Applications, Williams & Wilkins (1993).
Jaroszeski et al. (eds.), Flow Cytometry Protocols, Methods in Molecular Biology No. 91, Humana Press (1997).
Landy et al. (eds.), Clinical Flow Cytometry, Annals of the New York Academy of Sciences vol. 677 (1993).
Ormerod (ed.), Flow Cytometry: A Practical Approach, Oxford Univ. Press (1994).
Pawley (ed.), Handbook of Biological Confocal Microscopy, 2nd Edition, Plenum Press (1989).
Practical Shapiro, Flow Cytometry, 4th ed., Wiley-Liss (2003).

* cited by examiner

DYNAMIC DISPLAY OF MULTI-PARAMETER QUANTITATIVE BIOLOGICAL DATA

CROSS-REFERENCE TO RELATED APPLICATION(S)

This application claims priority to U.S. Provisional Application No. 62/534,004, filed on Jul. 18, 2017, which is incorporated by reference in its entirety. This application also claims priority to U.S. Provisional Application No. 62/608,241, filed on Dec. 20, 2017, which is incorporated by reference in its entirety. Any and all priority claims identified in the Application Data Sheet, or any correction thereto, are also hereby incorporated by reference under 37 C.F.R. § 1.57.

BACKGROUND

Technical Field

This disclosure relates to graphic displays, and in particular to dynamic displays of measurements for cells from a sample analyzed by a biological particle analyzer such as a flow cytometer.

Background

Particle analyzers, such as flow and scanning cytometers, are analytical tools that enable the characterization of particles on the basis of optical parameters such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection. A multiplicity of different particles or components may be simultaneously detected by using spectrally distinct fluorescent dyes to label the different particles or components. In some implementations, a multiplicity of photodetectors, one for each of the scatter parameters to be measured, and one for each of the distinct dyes to be detected are included in the analyzer. The data obtained comprise the signals measured for each of the light scatter parameters and the fluorescence emissions.

Cytometers may further comprise means for recording the measured data and analyzing the data. For example, data storage and analysis may be carried out using a computer connected to the detection electronics. For example, the data can be stored in tabular form, where each row corresponds to data for one particle, and the columns correspond to each of the measured parameters. The use of standard file formats, such as an "FCS" file format, for storing data from a flow cytometer facilitates analyzing data using separate programs and/or machines. Using current analysis methods, the data typically are displayed in 2-dimensional (2D) plots for ease of visualization, but other methods may be used to visualize multidimensional data.

The parameters measured using a flow cytometer typically include the excitation light that is scattered by the particle along a mostly forward direction, referred to as forward scatter (FSC), the excitation light that is scattered by the particle in a mostly sideways direction, referred to as side scatter (SSC), and the light emitted from fluorescent molecules in one or more channels (range of frequencies) of the spectrum, referred to as FL1, FL2, etc., or by the fluorescent dye that is primarily detected in that channel. Different cell types can be identified by the scatter parameters and the fluorescence emissions resulting from labeling various cell proteins with dye-labeled antibodies.

Both flow and scanning cytometers are commercially available from, for example, BD Biosciences (San Jose, Calif.). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1994); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed.), Handbook of Biological Confocal Microscopy, 2nd Edition, Plenum Press (1989), incorporated herein by reference.

The data obtained from an analysis of cells (or other particles) by multi-color flow cytometry are multidimensional, wherein each cell corresponds to a point in a multi-dimensional space defined by the parameters measured. Populations of cells or particles are identified as clusters of points in the data space. The identification of clusters and, thereby, populations can be carried out manually by drawing a gate around a population displayed in one or more 2-dimensional plots, referred to as "scatter plots" or "dot plots," of the data. Alternatively, clusters can be identified, and gates that define the limits of the populations, can be determined automatically. Examples of methods for automated gating have been described in, for example, U.S. Pat. Nos. 4,845,653; 5,627,040; 5,739,000; 5,795,727; 5,962,238; 6,014,904; 6,944,338; and 8,990,047, each incorporated herein by reference.

The parameters may include other measurements of a particle. For example, acoustic properties for a particle may be measured and included in the event data. The acoustic property may be directly measured for the particle itself or indirectly measured such as by detecting a change in an acoustic field when the particle interacts with the acoustic field.

For example, in one operational mode, a sample under study can be illuminated concurrently with a plurality of excitation frequencies, each of which can be obtained, e.g., by shifting the central frequency of a laser beam. More specifically, a plurality of sample locations can be concurrently illuminated by a laser beam that is generated by mixing a reference laser beam (herein also referred to as a local oscillator beam) with a plurality of radiofrequency-shifted laser beams such that each sample location is illuminated by the reference beam and one of the radiofrequency-shifted beams to excite a fluorophore of interest at that location, if present. In some embodiments, the reference beam can itself be generated via radiofrequency shifting of a laser beam. Thus, each spatial location of the sample can be "tagged" with a different beat frequency corresponding to a difference between the frequency of the reference beam and that of one of the radiofrequency-shifted beams. In other words, the fluorescence radiation emitted by the fluorophore will spatially encode the beat frequencies. The fluorescence emission can be detected and its frequency components can be analyzed to construct a fluorescence image of the sample.

As another example, a sample can be illuminated successively over a time interval by a laser beam at a plurality of excitation frequencies. In some such embodiments, the excitation frequencies can be obtained by applying a time-varying drive signal to an acousto-optic deflector (AOD), which receives a laser beam. In many embodiments, the laser beam has a frequency in the hundreds of terahertz (THz) range, e.g., in a range of about 300 THz to about 1000 THz. The drive signal applied to the AOD is typically in the radiofrequency range, e.g., in a range of about 10 MHz to about 250 MHz. The passage of the laser beam through the AOD generates a plurality of diffracted beams, each corresponding to a different diffraction order. While the zeroth diffracted beam exhibits no frequency shift relative to the frequency of the input laser beam, the higher-order diffracted beams exhibit a frequency shift relative to the frequency of the input laser beam corresponding to the frequency of the drive signal or a multiple thereof. In some embodiments, the first order diffracted beam having a frequency corresponding to the frequency of the input laser beam shifted by the drive signal is employed as the excitation beam for exciting a fluorophore of interest, if present in a sample under analysis. As the drive signal varies over time, the frequency and angular shift of the first-order diffracted beam also varies, thereby allowing the illumination of the sample at different excitation frequencies at different locations. The fluorescence emission, if any, from each illuminated location can be collected and analyzed to construct a fluorescence image of the sample. Additional features and systems for parameter detection including acoustic properties are described in U.S. Patent Publication No. 20170268981, which is hereby incorporated by reference.

As number of parameters that can be simultaneously measured by flow cytometers or other particle analyzers for a cell or sample increases due to factors such as new fluorochromes or detectors, the event data increases in size and complexity.

SUMMARY

The systems, methods, and devices of the disclosure each have several innovative aspects, no single one of which is solely responsible for the desirable attributes disclosed herein.

In one innovative aspect, a graphics control device for displaying a representation of multi-parametric data for cells on a graphical user interface is described. The data for a cell may include respective measurements for a set of different parameters. The graphics control device includes an input device port configured to receive, from an input device, a first selection indicating a subset of the cells. The graphics control device includes a plot generator. In response to receiving the first selection, the plot generator may be configured to dynamically display a base object. The plot generator may identify at least one of a size or a shape of the base object based at least in part on a size of the subset of the cells. The plot generator may dynamically display respective interactive controls. The plot generator may identify at least one of a size or a shape of an interactive control based at least in part on measurements for the subset of the cells for one of the set of different parameters. Each interactive control is displayed at respective points on the first base object.

The input device port may be configured to receive, from the input device, a second selection identifying: (i) a first interactive control associated with a first parameter included in the set of different parameters, and (ii) a second interactive control associated with a second parameter included in the set of different parameters. The plot generator may be configured to dynamically display a two-dimensional plot diagram of a portion of the measurements for the subset of cells. The two-dimensional plot diagram may include a first axis corresponding to measurements for the first parameter and a second axis corresponding to measurements of the second parameter. The two-dimensional plot diagram may include a graphical indicia for the cell at an intersection point for a first measurement for the first parameter for the cell and a second measurement for the second parameter for the cell.

In some implementations of the graphics control device, the input device port may receive, from the input device, a second selection. The second selection may identify: a first interactive control associated with a first parameter included in the different parameters represented in the data; a second interactive control associated with a second parameter included in the different parameters; or a third interactive control associated with a third parameter included in the different parameters. The plot generator may be configured to dynamically display a parallel coordinate plot diagram of the measurements for the subset of cells for the first parameter, the second parameter, and the third parameter identified by the second selection. The parallel coordinate plot may include: a first vertical axis for the first parameter, a second vertical axis for the second parameter, a third vertical axis for the third parameter, and a line connecting measurements for a cell on each vertical axis included in the parallel coordinate plot diagram.

The plot generator may be configured to display the interactive control in part by generating a height for the interactive control based on a median fluorescence intensity value for a marker on the subset of cells for the parameter associated with the interactive control.

The plot generator is optionally configured to display the interactive control in part by generating a display color for the interactive control based at least in part on a color of an exciting laser for a marker associated with the parameter represented by the interactive control.

The plot generator may be configured to display the interactive control in part by generating a display color for the interactive control based at least in part on a color of a fluorochrome for a marker associated with the parameter represented by the interactive control. The plot generator may be configured to display the interactive control in part by generating a display color for the interactive control based at least in part on a biological type associated with the parameter represented by the interactive control. In some implementations, the plot generator may be configured to selectively display an analytic overlay. The analytic overlay may be displayed over at least a portion of the interactive control, the analytic overlay having a length representing a calculated metric for the parameter represented by the interactive control. The calculated metric for the dimension may include at least one of: a robust standard variation, a standard deviation, an average, a mean, or a median of the measurements for the parameter.

In some implementations, the cell may be taken from a sample. In such implementations, the selection may include a gate identifying a range of measurements defining the subset of cells. The graphics control device may include a particle analyzer input port for receiving, from a particle analyzer (e.g., a flow cytometer or single-cell analysis system), measurements for a second cell from the sample. The plot generator may be further configured to determine the second cell is included in the range of measurements. Dynamically displaying the base object may include adjusting at least one of the size or the shape of the base object based on the size of the subset of cells. Dynamically displaying respective interactive controls may include adjusting at least one of the size or the shape of at least one interactive control further based at least in part on a second measurement for the second cell including in the measurements for the second cell.

In another innovative aspect, a computer-implemented method for displaying a representation of multi-parametric data for cells on a graphical user interface is provided. The data for a cell may include respective measurements for different parameters (e.g., markers). The computer-implemented method may be performed under the control of one or more computing devices. The method may include receiving, from an input device, a first selection indicating a subset of the cells. In response to receiving the first selection, the method may further include dynamically displaying a base object. At least one of a size or a shape of the base object is identified based at least in part on a size of the subset of the cells. In response to receiving the first selection, the method may further include dynamically displaying respective interactive controls. At least one of a size or a shape of an interactive control may be identified based at least in part on a measurement for a cell in one of the parameters, and wherein each interactive control is displayed at a point on the first base object.

The computer-implemented method may include receiving, from the input device, a second selection. The second selection may identify: (i) a first interactive control associated with a first parameter included in the parameters, and (ii) a second interactive control associated with a second parameter included in the parameters. Some implementations of the method may also include dynamically displaying a two-dimensional plot diagram of the measurements for the subset of cells. The two-dimensional plot diagram may include a first axis corresponding to measurements for the first parameter and a second axis corresponding to measurements of the second parameter. The two-dimensional plot diagram may include a graphical indicia for the cell at an intersection point for a first measurement for the first parameter for the cell and a second measurement for the second parameter for the cell.

Some implementations of the computer-implemented method may include receiving, from the input device, a second selection. The second selection may identify one or more of: a first interactive control associated with a first parameter included in the different parameters represented in the data; a second interactive control associated with a second parameter included in the different parameters; or a third interactive control associated with a third parameter included in the different parameters. The computer-implemented method may include dynamically displaying a parallel coordinate plot diagram of the measurements for the subset of cells for the first parameter, the second parameter, and the third parameter identified by the second selection. The parallel coordinate plot diagram may include: a first vertical axis for the first parameter; a second vertical axis for the second parameter; a third vertical axis for the third parameter; or a line connecting measurements for a cell on each vertical axis included in the parallel coordinate plot.

In one implementation of the computer-implemented method, displaying the interactive control may include generating a height for the interactive control based on a median fluorescence intensity value for a marker on the subset of cells for the parameter associated with the interactive control.

In one implementation of the computer-implemented method, displaying the interactive control may include generating a display color for the interactive control based at least in part on a color of an exciting laser for a marker associated with the parameter represented by the interactive control.

In one implementation of the computer-implemented method, displaying the interactive control may include generating a display color for the interactive control based at least in part on a color of a fluorochrome for a marker associated with the parameter represented by the interactive control.

In one implementation of the computer-implemented method, displaying the interactive control may include generating a display color for the interactive control based at least in part on a biological type associated with the parameter represented by the interactive control.

The computer-implemented method may include selectively displaying an analytic overlay. The analytic overlay may be displayed over at least a portion of the interactive control. The analytic overlay may have a length representing a calculated metric for the parameter represented by the interactive control. The calculated metric for the dimension comprises at least one of: robust standard variation, standard deviation, average, mean, or median.

In some implementations, the cell may be taken from a sample. The selection may include a gate identifying a range of measurements defining the subset of cells. The computer-implemented method may include receiving measurements, from a particle analyzer, for a second cell from the sample. The method may further include determining that the second cell is included in the range of measurements. Dynamically displaying the base object, in some implementations, may include adjusting at least one of the size or the shape of the base object based on the size of the subset of cells. Dynamically displaying respective interactive controls, in some implementations, may include adjusting at least one of the size or the shape of at least one interactive control further based at least in part on a second measurement for the second cell including in the measurements for the second cell.

In another innovative aspect, a system for displaying a representation of multi-parametric cellular data for cells on a graphical user interface is provided. The system includes a particle analyzer configured to detect, for each of the cells, measurements for respective markers. Examples of a particle analyzer include a flow cytometer or a single-cell analysis system. The system for displaying the representation of the multi-parametric cellular data further includes graphics processing circuitry in communication with the particle analyzer. The graphics processing circuitry is configured to receive, from an input device, a first selection indicating a subset of the cells. The graphics processing circuitry is further configured to, in response to receiving the first selection, dynamically display a base object. At least one of a size or a shape of the base object is identified based at least in part on a size of the subset of the cells. The graphics processing circuitry may also be configured to dynamically display respective interactive controls. At least one of a size or a shape of an interactive control is identified based at least in part on a measurement for a cell in one of the markers, and wherein each interactive control is displayed at a respective point on the first base object. Each point may be selected such that the interactive controls may be concurrently displayed with little or no overlap.

DETAILED DESCRIPTION

Figure 1:
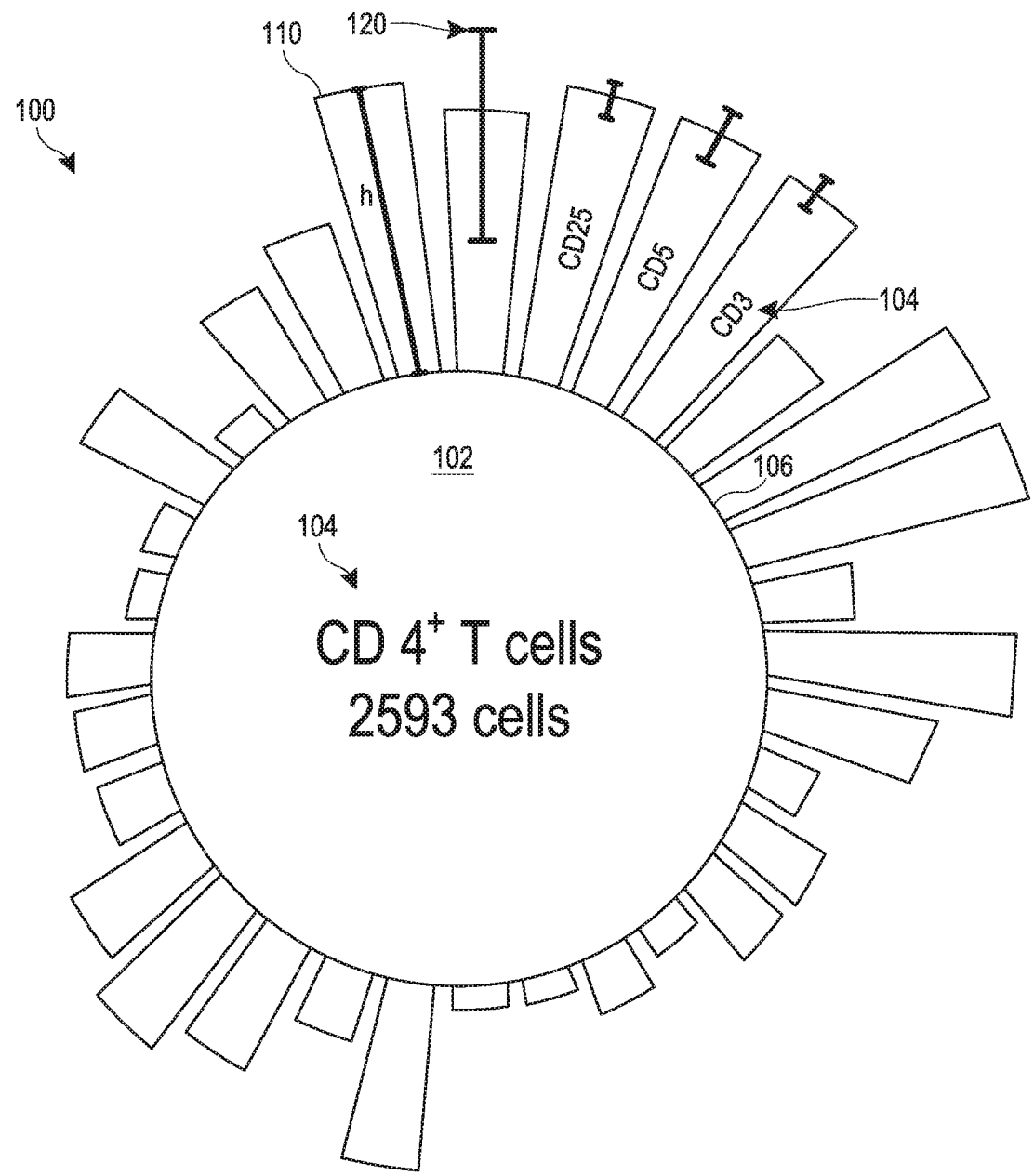
FIG. 1 shows an example of an interface for displaying multi-parametric data for a population of cells.

Previous solutions to multi-parametric data analysis for flow cytometry data typically involve the generating and displaying a large number of bivariate plots side by side or the generating and displaying scatterplot matrices. However, as the number of parameters measured increases, so does the combinations of scatterplots in the matrix, making the presentation and ultimate analysis of such data increasingly complex. For example, managing the layout of a graphical user interface includes allocating a limited display area for many combinations of the bivariate plots. The assessment of which combinations to show and where to show the selected combinations introduce complexity to the overall display system.

Parallel coordinate plots may be included to display or summarize items that have long list of components or attributes associated with them. These representations can be important to a user for assessing biological meaning to the measurements. However, parallel coordinate plots only provide a one-dimensional view of the data and can be difficult to represent complex relationships between events or parameters.

To address these problems with displaying multi-parameter quantitative biological data, new data visualization features are described that provide a fast and accurate tool for displaying visualizations of high parameter data. The graphics display techniques described require a specific structured graphical user interface paired with a prescribed functionality directly related to the graphical user interface's structure that is addressed to and resolves specific problems in the current visualization arts. The visualization features include graphically representing multiple parameters simultaneously with the associated statistical data for each parameter in an interactive way that maintains the contextual relationships between parameters and the related cell population. The visualization features could be used for displaying high parameter multi-color flow cytometry and genomic data sets.

The visualization may be represented as a "skyline plot" that provides a powerful glance of the population of interest by displaying, for example, an average cell representative of the mean or median cell of that population and all the parameters associated with it. Each parameter is visualized as a bar on top of a circle representing a cell. The size of the circle can be used to represent a variety of statistical parameters, including size, cell number within the gated cell population, density, and the like. Each bar corresponding to one parameter may have unique display characteristics such as color, label, or metric bar (e.g., error, deviation, median) to give a concise and instantaneous view of the heterogeneity of the expression of that parameter across the gated population. The skyline plot diagram can be used as an analysis tool for efficiently displaying the results of a cytometric experiment. The skyline plot diagram can be used as a querying tool. For example, portions of the skyline plot diagram may be interactive elements associated with via various computer gestures. A gesture may be received by the system and, in response to the gesture, the user interface may be adjusted to display or highlight cells having a desired level of expression for one or more identified parameters (e.g., an intracellular parameter, an extracellular parameter, a physical property parameter, etc.).

As used herein, "system," "instrument," "apparatus," and "device" generally encompass both the hardware (e.g., mechanical and electronic) and, in some implementations, associated software (e.g., specialized computer programs for graphics control) components.

As used herein, an "event" generally refers to the data measured from or about a single particle, such as a cell or synthetic particle. Typically, the data measured from a single particle include a number of parameters, including one or more light scattering parameters, and at least one fluorescence intensity parameters. Thus, each event is represented as a vector of parameter measurements, wherein each measured parameter corresponds to one dimension of the data space. The dimensions may relate to an intensity, an acoustic property, or other measurement for the cell or synthetic particle detected by a particle analyzer. In some biological applications, event data may correspond to quantitative biological data indicating expression of a particular protein or gene.

As used herein, a "population," or "subpopulation" of particles, such as cells or other particles, generally refers to a group of particles that possess optical properties with respect to one or more measured parameters such that measured parameter data form a cluster in the data space. Thus, populations are recognized as clusters in the data. Conversely, each data cluster generally is interpreted as corresponding to a population of a particular type of cell or particle, although clusters that correspond to noise or background typically also are observed. A cluster may be defined in a subset of the dimensions, e.g., with respect to a subset of the measured parameters, which corresponds to populations that differ in only a subset of the measured parameters.

As used herein, a "gate" generally refers to a boundary identifying a subset of data of interest. In cytometry, a gate may bound a group of events of particular interest. As used herein, "gating" generally refers to the process of defining a gate for a given set of data.

FIG. 1 shows an example of an interface for displaying multi-parametric data for a population of cells. The interface 100 provides a simultaneous view of measurements for a variety of parameters. The interface 100 may be referred to as a skyline plot. Each measurement may correspond to a particular marker detected for cells in a population. The interface 100 may be displayed for a selected subset of cells included in a set of flow cytometry data. The subset of cells may be identified using a gate from a two dimensional representation of the measurements (e.g., scatter plot). In such instances, measurements for the cells included in the gated area may be used to generate the interface 100. In this way, measurements for multiple dimensions may be simultaneously displayed based on a two dimensional input (e.g., the gate). The interface 100 may be generated by a graphics controller such the graphics controller described in FIG. 2 below.

As shown in FIG. 1, the interface includes a base object 102. The base area 102 may occupy a first display region 106 of the interface. The size of the first display region 106 may be dynamically determined using the number of cells included in the selected population. Accordingly, the larger the population of interest, the larger the first display region 106 may be. Equation (1) provides an example of how the area of the first display region 106 may be dynamically generated based on the number of cells and a size of a target display.

$$A = \pi (d - h_{max} - h_{max-1})^2 \qquad \text{Equation (1)}$$

where: A represents the area of the first display region;
d represents the total display area for the target display device;
$h_{max}$ represents the height of the largest interactive area; and
$h_{max-1}$ represents the height of the second largest interactive area.

The size of the target display may be provided in a request for the interface (e.g., with the identified set of cells). In some implementations, the size of the target display may be inferred from the request. For example, the request may include an identifier of the device type such as in a header field. The graphics controller may include a look up table or other data structure associating display area size with device types.

Descriptive region 104 may be included within the display region 106. The descriptive region 104 may include descriptive information about the selected cells. As shown in FIG. 1, the descriptive region 104 includes a textual description of the biological significance of the cells ("CD 4+ T cells") and a count (e.g., 2593) of the number of cells in the population. The descriptive information may be dynamically selected based on the size of the first display region 106. For example, where the base object 102 occupies a larger region, it may be possible to include additional descriptive information for the selected cell such as cell type, event number, parameter summary, etc. If the base object 102 occupies a smaller region than shown in FIG. 2, the count may be omitted.

Determining what descriptive information to display may be based on a hierarchy of descriptive information elements. The hierarchy may be specified at a system level or configured based on user input. The hierarchy may be stored in a memory accessible by the device generating the interface 100. Each descriptive information element may be associated with an estimated display area. The device generating the interface may allocate the descriptive region 104 and then identify which elements to include based on the estimated display areas for the elements. The elements may be ordered within the hierarchy to prioritized display of elements.

The interface 100 includes interactive areas such as an interactive area 110. Each interactive area corresponds to measurements for a parameter for the selected cells. For example, the interactive area 110 may represent a mean fluorescence intensity value for a particular marker. The height of the interactive area 110 (shown as h in FIG. 2) may represent the mean value. An interactive area may include an analytic overlay 120. The analytic overlay 120 may identify a calculated metric for the associated parameter such as error, deviation, robust standard variation, standard deviation, average, mean, median etc. The analytic overlay 120 may be displayed over at least a portion of the interactive control. In some implementations, a length of the analytic overlay 120 may be dynamically generated to represent the calculated metric.

An interactive area may include descriptive information 104. The descriptive information 104 may help identify the marker or measurement represented by the interactive area. The descriptive information 104 may be stored in a memory accessible by the device rendering the interface 100. The descriptive information 104 may be associated with a marker or measurement type identified in the measurements for the cells. Using the measurement information for the selected cells, an appropriate description may be identified for display. Furthermore, this allows suppression of the display of descriptive information for markers that are not present in the selected population.

The interactive area 110 may be dynamically rendered to include a color corresponding to the marker associated with the measurement such as, for example, CD4-FITC. The color for the interactive area 110 may also be adjusted to reflect additional properties for the parameter. For example, the hue, the brightness, the opacity, or other property of the color may be dynamically adjusted. The adjustment may be based on a number of measurements for cells corresponding to the mean intensity. The adjustment may be based on the number measurements for cells corresponding to the mean intensity as compared to the total number of cells in the selected population. Equation (2) below provides one expression for dynamically generating a scaling factor for a color property.

$$s = \frac{\sum_{c=0}^{n} |m_c - m_{mean}|}{n} \qquad \text{Equation (2)}$$

where: s represents the scaling factor for the color property;
n represents the size of the cell population;
$m_c$ represents the measurement for cell c in the cell population for a marker; and
$m_{mean}$ represents the mean for the measurements for the cell population for the marker.

In some implementations, the interactive areas may be used to display additional views for the cell measurements. For example, two interactive areas may be selected for presentation via a two-dimensional plot diagram such as a scatter plot diagram for the selected measurements. The two-dimensional plot diagram may include a first axis corresponding to measurements for the first parameter and a second axis corresponding to measurements of the second parameter. The two-dimensional plot diagram may include one or more graphical indicia for a cell at an intersection point for a first measurement for the first parameter for the cell and a second measurement for the second parameter for the cell. The graphical indicia may be colored to correspond with the color of the associated interactive control. In this way, a cognitive contextual link may be formed between the multi-dimensional skyline view and the two-dimensional plot.

As another example, three or more interactive areas may be selected for presentation via a multi-dimensional plot diagram such as a parallel coordinate plot diagram. The parallel coordinate plot diagram may include an axis for the parameter associated with each selected interactive area and a line connecting measurements for a cell on each vertical axis included in the parallel coordinate plot.

Figure 2:
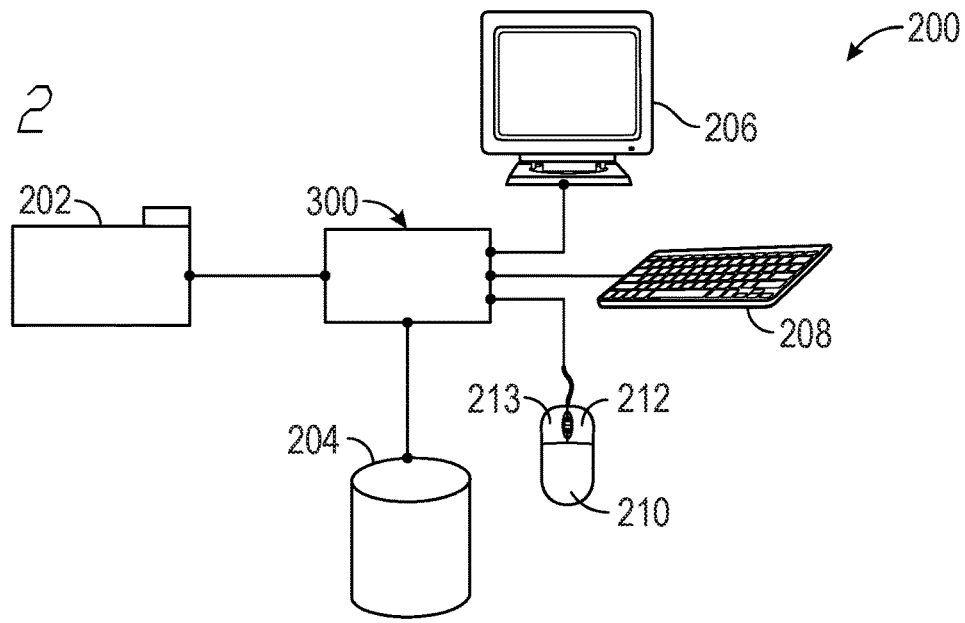
FIG. 2 shows a functional block diagram for one example of a graphics control system for analyzing and displaying cytometric events.

FIG. 2 shows a functional block diagram for one example of a graphics control system for dynamically displaying flow cytometry data. A graphics controller 300 included in the system 200 may be configured to implement processes for generating the interface 100 shown in FIG. 1.

A flow cytometer 202 may be configured to acquire flow cytometric events. For example, flow cytometer 202 may generate flow cytometric event data. The flow cytometer 202 may be configured to provide flow cytometric events to the graphics controller 300. A data communication channel may be included between the flow cytometer 202 and the graphics controller 300. The flow cytometric events may be provided to the graphics controller 300 via the data communication channel.

Aspects of the description may specifically reference flow cytometers and flow cytometry event data. In some embodiments, other particle analyzers may generate the event data corresponding to other quantitative biological data such as data indicating expression of a particular protein or gene. For example, the event data may indicate the presence of an mRNA sequence within a cell or across a mixed population of cells. The event data may identify an absolute number of gene transcripts of a transcriptome for a cell or cells. Presentation of the event data may be adjusted per cell or per gene expression to provide different perspectives on populations of event data of particular interest (e.g., associated with a particular mRNA sequence, taken from a specific cell, etc.). The event data may be generated using massively parallel single cell analytic features such as those described in U.S. Pat. No. 9,567,645 which is hereby incorporated by reference in its entirety. One commercially available single-cell analysis system is the Becton, Dickinson Rhapsody™ hardware by Becton, Dickinson and Company of Franklin Lakes, N.J. The features discussed may be applied to visualize other or additional quantitative multi-parameter biological data such as that associated with gene expression.

The flow cytometric data may be received in real-time as measurements are collected by the flow cytometer 202. In some implementations, the flow cytometric data may be received via a bulk transfer operation between the flow cytometer 202 and the graphics controller 300. The flow cytometric data received from the flow cytometer 202 may include flow cytometric event data (e.g., measurements of detected fluorescence for one or more markers for each cell included in a sample). The graphics controller 300 may be configured to dynamically generate and display an interface showing flow cytometric events to a display device 206. The display device 206 may be implemented as a monitor, a tablet computer, a smartphone, or other electronic device configured to present graphical interfaces.

The graphics controller 300 may be configured to receive a gate selection signal identifying the gate from a first input device. For example, the first input device may be implemented as a mouse 210. The mouse 210 may initiate a gate selection signal to the graphics controller 300 identifying the gate to be displayed on or manipulated via the display device 206 (e.g., by clicking on or in the desired gate when the cursor is positioned there). The gate may also be used to identify the population for displaying additional or alternative interfaces such as the interface 100.

The graphics controller 300 may be configured to detect interactions with the interface 100. The second input device may be implemented as a keyboard 208. The keyboard 208 may control changes in plot visualization by sending a signal identifying a triggering event to the graphics controller 300. For example, activation of a specific key or group of keys on the keyboard 208 may generate a specific interaction. In response to the interaction, the graphics controller 300 may be configured to replace or update the interface(s) displayed on the display device 206.

In displaying the interface 100, the graphics controller 300 may specify interactions for specific regions. For example, the base object may respond to a mouse scroll interaction when the cursor is within the first display region. The response may include changing the selected population to a different gated population and rendering a new version of the interface 100 based on the cytometric data for the different gated population. As another example, an interactive region corresponding to a measurement may be associated with a selection interaction. When the interactive region is selected, additional information about the measurements or marker associated therewith may be displayed such as metrics for the measurements for cells, error rate, marker spectral range, or information regarding the cytometric experiment such as entrainment, average flow rate, initial sample size, total cells measured from the sample, sorting information, or the like. Other example interactions include rotation of the interface 100. Upon detecting a rotation interaction, the interface 100 may adjust the parameter ordering, change one or more color used to render the interface 100 or element included therein, introduce a third dimension whereby each interactive area may be presented as a three-dimensional object. The third dimension may be used to compare the parameter associated with the interactive area and a second parameter. The rotation interaction may cycle the population of interest. For example, the flow cytometry data may include multiple gated populations of interest. As the interface 100 is rotated, a different population of interest may be selected and used to generate the interface 100 as described.

An input device may be implemented as one or more of the mouse 210, the keyboard 208, or other means for providing an input signal to the graphics controller 300 such as a touchscreen, a stylus, an optical detector, or a voice recognition system. Some input devices may include multiple inputting functions. In such implementations, the inputting functions may each be considered an input device. For example, as shown in FIG. 2, the mouse 210 includes a right mouse button 212 and a left mouse button 113, each of which may generate unique interactions with the display.

An interaction may cause the graphics controller 300 to alter the manner in which the data is displayed or which portions of the data is actually displayed on the display device 206 or both at the same time.

The graphics controller 300 may be connected to a storage device 204. The storage device 204 may be configured to receive and store flow cytometric events from the graphics controller 300. The storage device 204 may also be configured to receive and store flow cytometric event data from the graphics controller 300. The storage device 204 may be further configured to allow retrieval of flow cytometric events and flow cytometric event data by the graphics controller 300.

A display device 206 may be configured to receive display data from the graphics controller 300. The display data may comprise plots of flow cytometric events and gates outlining sections of the plots. The display device 206 may be further configured to alter the information presented according to input received from the graphics controller 300 in conjunction with input from the flow cytometer 202, the storage device 204, the keyboard 208, or the mouse 210.

Figure 3:
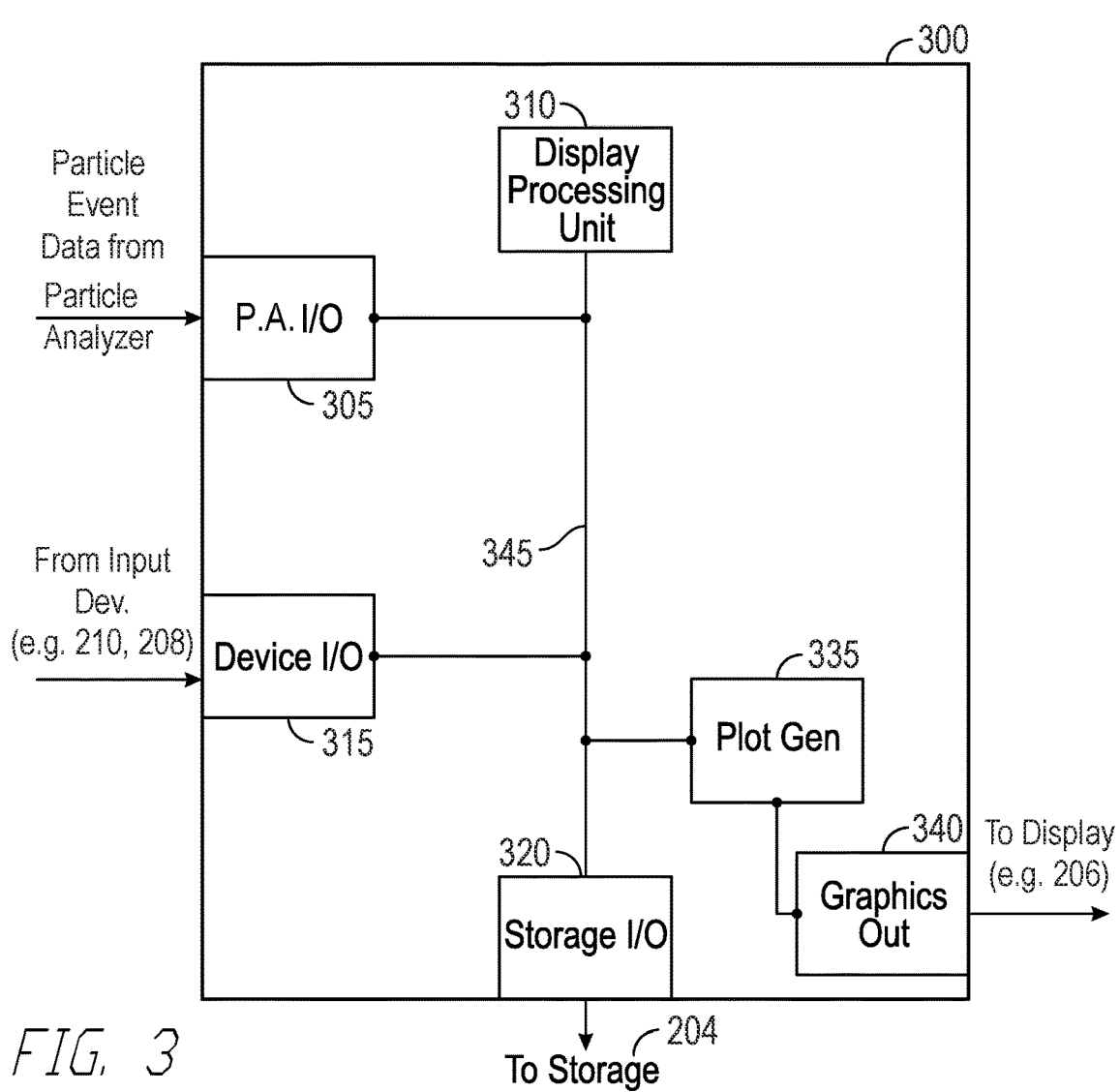
FIG. 3 shows a functional block diagram of an example of a graphics controller.

FIG. 3 shows a functional block diagram of an example of a graphics controller. The graphics controller 300 shown in FIG. 3 may be included in the system 200 shown in FIG. 2. The graphics controller 300 may be implemented as a specially configured device for dynamically displaying flow cytometry data during or after cytometric data processing. In some implementations, the graphics controller 300 may be integrated with the flow cytometer 202, a display device 206 (e.g., tablet computer, laptop computer, desktop computer), or other electronic hardware.

The graphics controller 300 may include a particle analyzer input/output (I/O) interface 305. The particle analyzer input/output interface 305 may be configured to receive cytometric event data from a particle analyzer, such as the flow cytometer 202 shown in FIG. 2. The particle analyzer I/O interface 305 may be a hardware interface providing a path for the event data to be received by the graphics controller 300. For example, the particle analyzer input/output interface 305 may be implemented as a network interface, a Universal Serial Bus interface, a serial data communication interface, memory access device, or other machine-to-machine communication interface. The data may be received in a standardized, machine readable format such as a comma separated list, a token separated list, mark-up language document, or a spreadsheet.

The particle event data received by the graphics controller 300 via the particle analyzer input/output interface 305 may be stored in a storage device such as the storage device 204 shown in FIG. 2. The graphics controller 300 may include a storage input/output (I/O) interface 320 to facilitate storage and retrieval of data to and from a storage device. For example, the storage I/O interface 320 may be implemented as a network interface, a Universal Serial Bus interface, a serial data communication interface, memory access device, or other machine-to-machine communication interface. In some implementations, the storage I/O interface 320 may be configured to generate queries to retrieve information requested by an element of the graphics controller 300. Such queries may be in a standardized query language such as Structured Query Language (SQL). In some implementations, the storage I/O interface 320 may be configured to generate storage commands to persist data in the storage device. SQL update or insert commands are examples of storage commands generated by the storage I/O interface 320.

A display processing unit 310 is shown in FIG. 3. The display processing unit 310 may coordinate the activities of the graphics controller 300. For example, the display processing unit 310 may receive a signal that data has been received via the particle analyzer I/O interface 305. Upon detecting the signal, the display processing unit 310 may transmit an instruction to route the data to the storage I/O interface 320 for storage. The display processing unit 310 may coordinate the activities according to a preconfigured set of machine readable instructions.

The graphics controller 300 shown in FIG. 3 also includes a device input/output (I/O) interface 315. The device I/O interface 315 receives signals from input devices such as a mouse or keyboard. The display processing unit 310 may detect an input signal and adjust a display as will be described in further detail. One input signal may include a message to begin displaying flow cytometric data. The input signal may include an identifier for the cytometric experiment for which data should be displayed. Using this identifier, the event data may be retrieved such as via the storage I/O interface 320 or from a particle analyzer via the particle analyzer I/O interface 305.

The graphics controller 300 may include a plot generator 335. The plot generator 335 may be configured to generate a computer displayable graphic representation of the event data such as the skyline plot diagram shown in FIG. 1. The plot generator 355 may be triggered by the graphics controller 300 to generate the plot. The triggering event may include receipt of particle data or experiment data via the particle analyzer I/O interface 305. In some implementations, the triggering event may include the selection of a group of cells (e.g., a gated population) received via the device I/O interface 315.

The plot generator 335 may then generate a specific interface tailored to the data and the target display device. The representation may then be provided to a display via a graphics output interface 340. The graphics output interface may be a video graphics array (VGA) interface, a high definition multimedia interface (HDMI), a wired or wireless network interface, or other communication means configured to provide graphics data, directly or indirectly, to a display device.

The elements included in the graphics controller 300 may be coupled by a bus 345. The bus 345 may be a data bus, communication bus, or other bus mechanism to enable the various components of the graphics controller 300 to exchange information. It will further be appreciated that while different elements have been shown, multiple features may be combined into a single element, such as the plot generator 335 and the display processing unit 310. Furthermore, additional elements may be included in the graphics controller 300 to support the features described. For example, a power source is not shown but may be included to provide power for the graphics controller 300. This can allow the graphics controller 300 to operate as a standalone graphics control hub to receive data from one or more particle analyzers, receive inputs from one or more input devices, and display interfaces one or more display devices.

Figure 4:
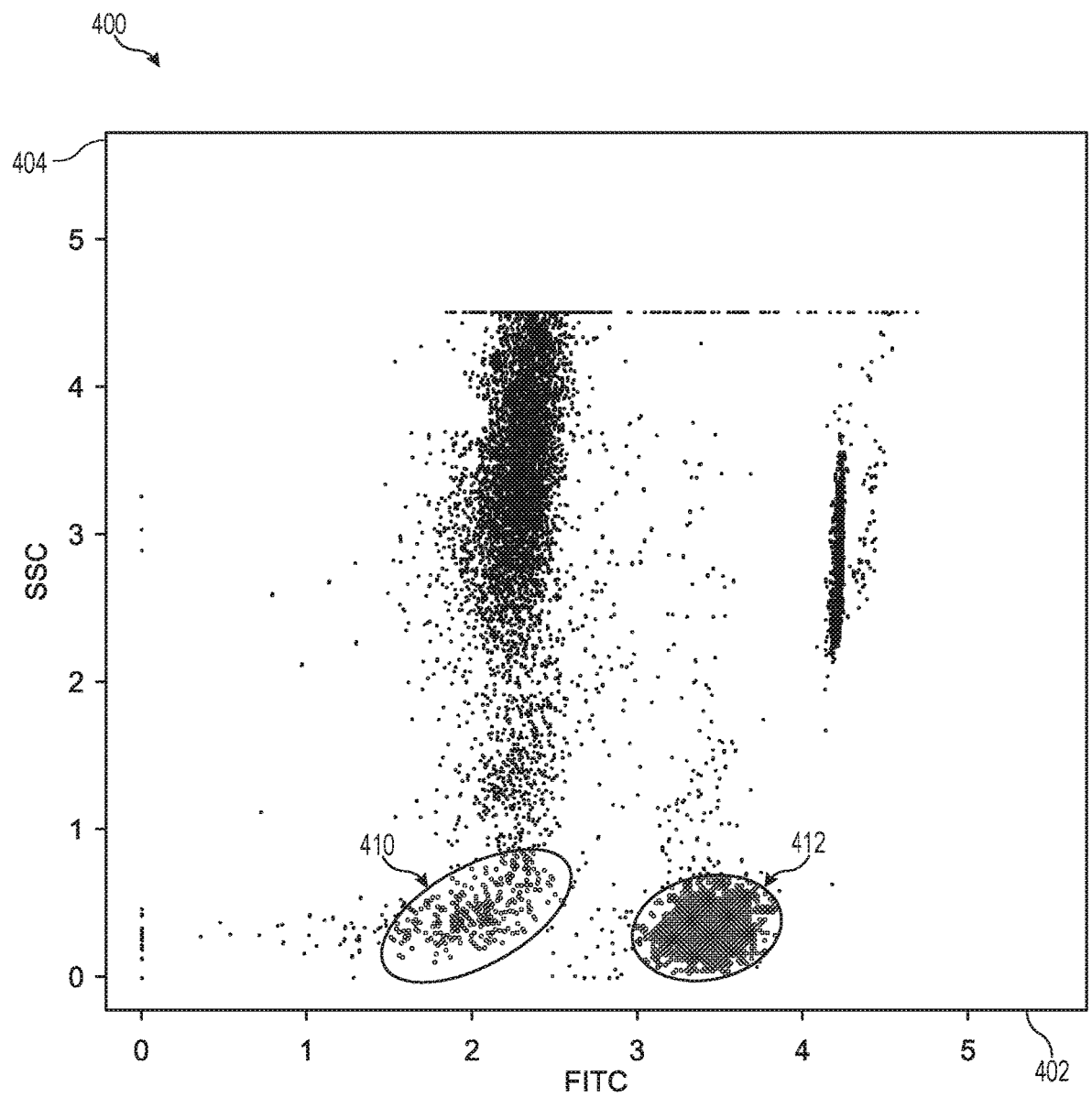
FIG. 4 shows an example of a scatter plot diagram including gates.

FIG. 4 shows an example of a scatter plot diagram including gates. The dot-plot 400 displays a scatter plot diagram of the events along an x-axis 402 and a y-axis 404. The x-axis 402 illustrates the parameter of interest. In the example shown in FIG. 4, the x-axis 402 represents light intensity for FITC labeled cells. The y-axis 404 shows the side scatter count (SSC). The side scatter count may be referred to as events or event count. The dot-plot 400 is one example of a two-dimensional representation of cytometric data that may be generated by the plot generator 335.

The plot 400 can be displayed such that several populations of cells are identified. Each population may be represented using a unique color. Each dot in a dot-plot diagram may represent a biological object, often a cell. Geometrical borders may be provided around specific populations. Such borders are called gates, and the processing of establishing or adjusting them is gating. FIG. 4 shows two gates, gate 410 and gate 412. The gating can be performed automatically by software algorithms, or manually by a human; or it may be initially performed automatically and then adjusted manually. In manual gating, the operator draws or adjusts the gates by clicking the plot diagram with computer mouse and dragging the mouse.

In some implementations, a gate may be selected for further processing. For example, the gate 410 may be selected to perform an operation on the cells included in the gate 410. One operation may be to generate a multi-parametric interface showing more than two parameters for the selected cells. One example of such a multi-parametric interface is the interface 100 shown in FIG. 1. The graphics controller 300 may receive a signal indicating the selection of the gate 410 along with an action (e.g., display multi-parametric interface). The graphics controller 300 may interpret the action and generate the interface 100 based on the measurements for the cells included in the gated region.

Figure 5:
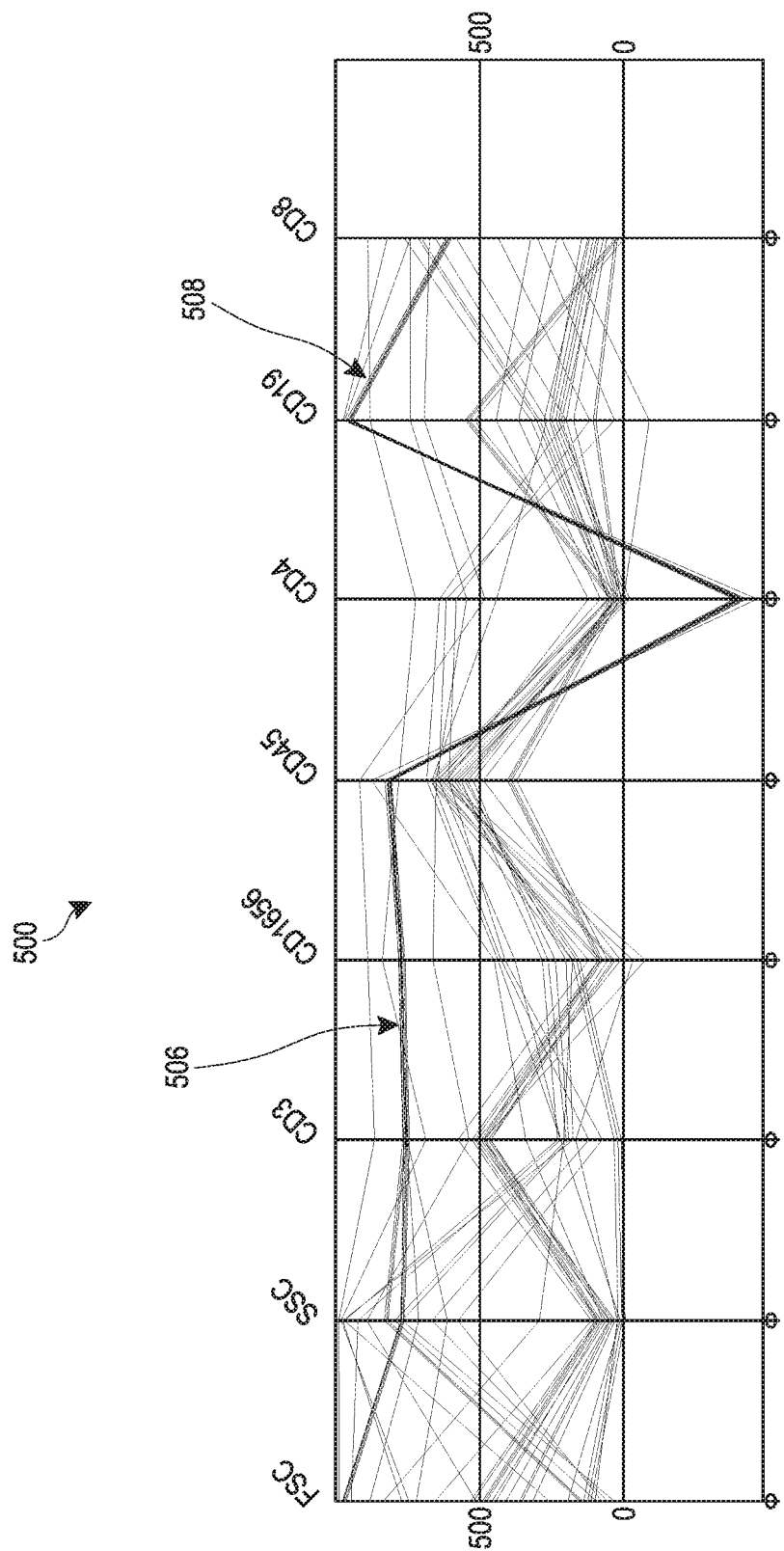
FIG. 5 shows an example of a parallel coordinate plot diagram.

FIG. 5 shows an example of a parallel coordinate plot diagram. The parallel coordinate plot (PCP) diagram includes a vertical axis for a variety of markers. As shown in FIG. 5, measurements for nine markers (FSC, SSC, CD3, CD1656, CD45, CD4, CD19, and CD8) are presented. Each cell is represented by a line 506 where the line for the cell crosses a vertical axis at the measured value for the marker associated with the vertical axis. As shown in FIG. 4, the measured value corresponds to a fluorescent intensity for the cell for the associated marker. A peak 508 indicates a group of cells with measurements that indicate a positive expression for the associated marker. The cells associated with intensities at or near the peak 508 may be grouped together for gating. In some implementations, a user may select a portion of the PCP diagram such as the peak 508. The selection may include clicking the peak 508 or drawing a geometric shape that encompasses the peak 508. The cells included in the selection may be used to define a population of interest for generating the interface 100 shown in FIG. 1.

Figure 6:
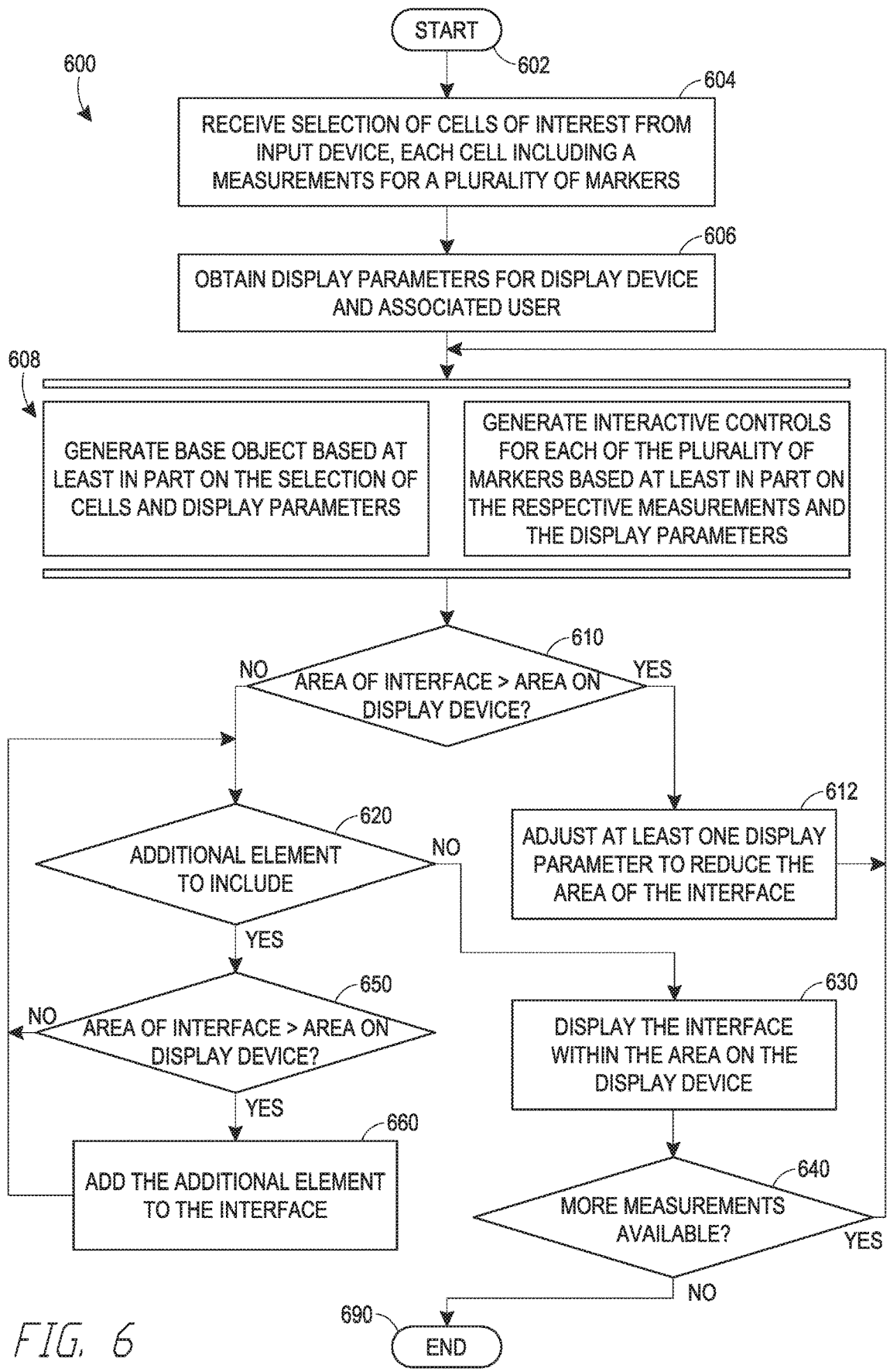
FIG. 6 is a process flow diagram of an example method of displaying a representation of multi-parametric flow cytometry data for cells on a graphical user interface.

FIG. 6 is a process flow diagram of an example method of displaying a representation of multi-parametric flow cytometry data for cells on a graphical user interface. The method 600 may be implemented in whole or in part by one or more of the devices described, such as those shown in FIG. 1 or FIG. 2. The method 600 illustrates how a dynamic interface is generated and displayed for a selected group of cells. The interface may include a representation of multi-parametric flow cytometry data for cells on a graphical user interface. The flow cytometry data for a cell may include respective measurements for a set of parameters (e.g., markers).

The method 600 begins at block 602. At block 604, the graphics controller may receive a first selection indicating a subset of cells may be received from an input device. The selection of cells may be identified by a gate from a two dimensional plot, such as shown in FIG. 4. The selection of cells may be identified by selecting a portion of a PCP diagram such as shown in FIG. 5. The input device may include one or more of a mouse, a keyboard, a touchscreen, a stylus, an optical detector, or a voice recognition system. Each cell included in the selection may be associated with flow cytometry data such as measurements for a set of parameters.

At block 606, the graphics controller may obtain display parameters for a display device that will present the interface and a user associated with the display device. The display parameters may be obtained from information included with the selection received at block 604 such as a user identifier or device identifier. The graphics controller may use one or more of the identifiers to retrieve user display parameters or device display parameters. A display parameter may identify a visual characteristic for the interface such as descriptive information to include in the interface, font, font size, color scheme, ordering of markers, shape for a base object, shape for the interactive controls, or the like. The graphics controller may retrieve the display parameters from memory accessible by the graphics controller such as the storage device 204.

At block 608, the plot generator included in the graphics controller may generate a base object and interactive controls for the interface. The base object may be generated using the selection of cells and the display parameters obtained at block 604.

The interactive controls may include an interactive control for each marker represented in the flow cytometry data. For example, using the PCP diagram from FIG. 5, assuming the PCP plot 500 shows all the flow cytometry data, at block 608, eight interactive controls would be generated.

The generating of the base object and the interactive controls may be performed in parallel. In some implementations, the generation of the base object may depend on the interactive controls or the interactive controls may depend on the base object. For example, as discussed with reference to Equation (1), the width if a circular base object may depend on the height of the largest interactive control. In such instances, the generating at block 608 may be an iterative process.

The iteration may be controlled based on a determination at block 610 as to whether the area of the interface including the base object and interactive controls exceeds the area on the display device that will present the interface. If the determination at block 610 is negative, at block 612, the graphics controller may adjust at least one display parameter to reduce the area of the interface. Adjusting the display parameter may include removing descriptive information from the interface, adjusting the font or font size used in the interface, scaling the base object and interactive controls included interface, or other area reduction processing. An amount of adjustment may be determined based on a comparison between the area of the interface and the allocated area on the display device. For example, if the area of the interface exceeds the allocated area by 10%, the interface may be scaled by 10% or the font size reduced by 10%. Once the display parameter(s) are adjusted, the method 600 may return to block 608 to re-generate the interface elements using the adjusted display parameters.

Returning to block 610, if the interface does not exceed the allocated area on the display device, the method 600 may proceed to block 620. At block 620, the plot generator may determine whether additional elements may be added to the interface. The determination may be based on a listing of optional display elements such as metrics for the selected population, metadata for the selected population, metadata for the flow cytometer that collected the measurements, or other information related to the flow cytometry data.

If the determination at block 620 is negative, at block 630, the graphics output interface may transmit the interface for display the interface on the display device. Displaying at block 630 may include transmitting a standardized, machine-readable message to the display device including the information for presenting the interface. The information may include an area on the display to render the interface, color information, geometric shape definitions for the base object or interactive controls, one or more interaction events for the interactive controls, and the like.

If the determination at block 620 is affirmative and additional elements are available for inclusion, at block 650, a determination is made as to whether the area of the interface, with an additional element, is within the area allocated by the display device for the interface. If the determination at block 620 is affirmative, at block 660, the plot generator may add the additional element to the interface. The method 600 may then return to block 620 to determine whether any other elements can be added.

Returning to block 650, if it is determined that the area exceeds the allocated area, the method 600 may return to block 620 to determine whether any other elements can be added.

After displaying the interface on the display device, at block 640 the graphics controller may determine whether more measurements are available for this flow cytometry experiment. The availability of measurements may be assessed by interrogating the flow cytometry measurements for the experiment. Based on information for the measurements such as a timestamp, it may be determined that additional measurements were received after the interface was generated. The determination at block 640 may be determined by the cytometry interface detecting the receipt of additional measurements. The cytometry interface may assess an identifier for the experiment included with data received from the flow cytometer. Where the identifier is associated with previous data used to generate the interface, the determination at block 640 may be affirmative. In the case where the determination at block 640 is affirmative, the method 600 may return to block 608 to generate the interface a new in consideration of the prior and additional measurements. If the determination at block 640 is negative, the method 600 ends at block 690.

The interface described informs the user in a more convenient and efficient manner than existing systems. Researchers gain a significant advantage by seeing multiple parameters in a single view because they can see trends the relationships between different markers for a group of cells. Presenting the parameters as described retains the contextual relationship between the multiple dimensions on a single interface.

When the interface is updated in real time, the progression of an experiment can be observed and used to identify adjustments to the flow cytometer or particle analyzing device. For example, trends in the measurements for cells of interest, the function of the flow cytometer, or other relevant characteristics are more easily identifiable by the user through the use of the present invention. Furthermore, the interface described provides a concise and efficient representation of large sets of multi-parameter data such as those associated with a flow cytometry experiment or single-cell gene expression experiment.

The base object representing a population of cells may be a three dimensional object. For example, the base object may be displayed as an avatar representing the cell population. The avatar may have display properties that can be adjusted according to the measurements included in the group of cells. For example, a skyline plot diagram could be considered as an avatar for the cells, in lieu of a microscopic image, that could show all protein expressions simultaneously. The display may be provided in a virtual reality (VR) environment or augmented reality (AR) environment allowing interactive searching through the multi-dimensional flow cytometry data. Because the skyline plot diagram may represent three dimensions of data, the ability to maintain orientation in such AR or VR environments is improved.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. Also, "determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein a "user interface" (also referred to as an interactive user interface, a graphical user interface or a UI) may refer to a network based interface including data fields and/or other controls for receiving input signals or providing electronic information and/or for providing information to the user in response to any received input signals. A UI may be implemented in whole or in part using technologies such as hyper-text mark-up language (HTML), FLASH™, JAVA™, .NET™, web services, or rich site summary (RSS). In some implementations, a UI may be included in a standalone client (for example, thick client, fat client) configured to communicate (e.g., send or receive data) in accordance with one or more of the aspects described.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the term "message" encompasses a wide variety of formats for communicating (e.g., transmitting or receiving) information. A message may include a machine readable aggregation of information such as an XML, document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, a phrase referring to "at least one of" a list of items refers to any combination of those items, including single members. As an example, "at least one of: a, b, or c" is intended to cover: a, b, c, a-b, a-c, b-c, and a-b-c.

Those of skill in the art would further appreciate that the various illustrative logical blocks, modules, circuits, and algorithm steps described in connection with the embodiments disclosed herein may be implemented as specially configured electronic hardware, computer software, or combinations of both. To clearly illustrate this interchangeability of hardware and software, certain illustrative components, blocks, modules, circuits, and steps may be described in terms of their functionality. Whether such functionality is implemented as hardware or software depends, at least in part, upon the particular application and design constraints imposed on the overall system. Skilled artisans may implement the described functionality in varying ways for each particular application, but such implementation decisions should not be interpreted as causing a departure from the scope of the present invention.

The techniques described herein may be implemented in hardware, software, firmware, or any combination thereof. Such techniques may be implemented in any of a variety of devices such as specifically programmed event processing computers, wireless communication devices, flow cytometers, or integrated circuit devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable medium may be a non-transitory storage medium. The techniques additionally, or alternatively, may be realized at least in part by a computer-readable communication medium that carries or communicates program code in the form of instructions or data structures and that can be accessed, read, and/or executed by a computing device, such as propagated signals or waves.

The program code may be executed by a specifically programmed graphics processor, which may include one or more processors, such as one or more digital signal processors (DSPs), configurable microprocessors, an application specific integrated circuits (ASICs), field programmable logic arrays (FPGAs), or other equivalent integrated or discrete logic circuitry. Such a graphics processor may be specially configured to perform any of the techniques described in this disclosure. A combination of computing devices, e.g., a combination of a DSP and a microprocessor, a plurality of microprocessors, one or more microprocessors in conjunction with a DSP core, or any other such configuration in at least partial data connectivity may implement one or more of the features describe. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding messages, or incorporated in a specialized graphic control card.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Various embodiments of the invention have been described. These and other embodiments are within the scope of the following claims.

What is claimed is:

1. A graphics control device for displaying a representation of multi-parametric data for cells on a graphical user interface, wherein the data for a cell includes respective measurements for a plurality of parameters, the graphics control device comprising:
an input device port configured to receive, from an input device, a first selection indicating a subset of the cells; and
a plot generator configured to, in response to receiving the first selection:
dynamically display a base object, wherein at least one of a size or a shape of the base object is identified based at least in part on a size of the subset of the cells, and
dynamically display respective interactive controls, wherein at least one of a size or a shape of an interactive control is identified based at least in part on measurements for the subset of the cells for one of the plurality of parameters, and wherein each interactive control is displayed at respective points on the base object.

2. The graphics control device of claim 1, wherein the input device port is further configured to receive, from the input device, a second selection identifying: (i) a first interactive control associated with a first parameter included in the plurality of parameters, and (ii) a second interactive control associated with a second parameter included in the plurality of parameters; and
wherein the plot generator is further configured to dynamically display a two-dimensional plot diagram of a portion of the measurements for the subset of the cells, wherein the two-dimensional plot diagram includes a first axis corresponding to measurements for the first parameter and a second axis corresponding to measurements of the second parameter, and wherein the two-dimensional plot diagram includes a graphical indicia for the cell at an intersection point for a first measurement for the first parameter for the cell and a second measurement for the second parameter for the cell.

3. The graphics control device of claim 1, wherein the input device port is further configured to receive, from the input device, a second selection identifying:
(i) a first interactive control associated with a first parameter included in the plurality of parameters,
(ii) a second interactive control associated with a second parameter included in the plurality of parameters, and
(iii) a third interactive control associated with a third parameter included in the plurality of parameters; and
wherein the plot generator is further configured to dynamically display a parallel coordinate plot diagram of the measurements for the subset of the cells for the first parameter, the second parameter, and the third parameter identified by the second selection, wherein the parallel coordinate plot diagram includes:
(i) a first vertical axis for the first parameter,
(ii) a second vertical axis for the second parameter,
(iii) a third vertical axis for the third parameter, and
(iv) a line connecting measurements for a cell on each vertical axis included in the parallel coordinate plot.

4. The graphics control device of claim 1, wherein the plot generator is configured to display the interactive control in part by:
generating a height for the interactive control based on a median fluorescence intensity value for a marker on the subset of the cells for the parameter associated with the interactive control.

5. The graphics control device of claim 1, wherein the plot generator is configured to display the interactive control in part by:
generating a display color for the interactive control based at least in part on a color of an exciting laser for a marker associated with the parameter represented by the interactive control.

6. The graphics control device of claim 1, wherein the plot generator is configured to display the interactive control in part by:

generating a display color for the interactive control based at least in part on a color of a fluorochrome for a marker associated with the parameter represented by the interactive control.

7. The graphics control device of claim 1, wherein the plot generator is configured to display the interactive control in part by:
generating a display color for the interactive control based at least in part on a biological type associated with the parameter represented by the interactive control.

8. The graphics control device of claim 1, wherein the plot generator is configured to selectively display an analytic overlay, wherein the analytic overlay is displayed over at least a portion of the interactive control, the analytic overlay having a dimension representing a calculated metric for the parameter represented by the interactive control.

9. The graphics control device of claim 8, wherein the calculated metric for the dimension comprises at least one of: robust standard variation, standard deviation, average, mean, or median.

10. The graphics control device of claim 1, wherein the cell is taken from a sample, wherein the selection comprises a gate identifying a range of measurements defining the subset of the cells;
wherein the graphics control device comprises a particle analyzer input port for receiving, from a particle analyzer, measurements for a second cell from the sample; and
wherein the plot generator is further configured to:
determine the second cell is included in the range of measurements,
wherein dynamically displaying the base object comprises adjusting at least one of the size or the shape of the base object based on the size of the subset of the cells, and
wherein dynamically displaying respective interactive controls comprises adjusting at least one of a size or a shape of at least one interactive control further based at least in part on a second measurement for the second cell including in the measurements for the second cell.

11. A computer-implemented method for displaying a representation of multi-parametric data for cells on a graphical user interface, wherein the data for a cell includes respective measurements for a plurality of parameters, the computer-implemented method comprising:
under the control of one or more computing devices:
receiving, from an input device, a first selection indicating a subset of the cells; and
in response to receiving the first selection:
dynamically displaying a base object, wherein at least one of a size or a shape of the base object is identified based at least in part on a size of the subset of the cells, and
dynamically displaying respective interactive controls, wherein at least one of a size or a shape of an interactive control is identified based at least in part on a measurement for a cell in one of the plurality of parameters, and wherein each interactive control is displayed at a point on the base object.

12. The computer-implemented method of claim 11, further comprising:
receiving, from the input device, a second selection identifying: (i) a first interactive control associated with a first parameter included in the plurality of parameters, and (ii) a second interactive control associated with a second parameter included in the plurality of parameters; and
dynamically displaying a two-dimensional plot diagram of the measurements for the subset of the cells, wherein the two-dimensional plot diagram includes a first axis corresponding to measurements for the first parameter and a second axis corresponding to measurements of the second parameter, and wherein the two-dimensional plot diagram includes a graphical indicia for the cell at an intersection point for a first measurement for the first parameter for the cell and a second measurement for the second parameter for the cell.

13. The computer-implemented method of claim 11, further comprising:
receiving, from the input device, a second selection identifying:
(i) a first interactive control associated with a first parameter included in the plurality of parameters;
(ii) a second interactive control associated with a second parameter included in the plurality of parameters; and
(iii) a third interactive control associated with a third parameter included in the plurality of parameters; and
dynamically displaying a parallel coordinate plot diagram of the measurements for the subset of the cells for the first parameter, the second parameter, and the third parameter identified by the second selection, wherein the parallel coordinate plot diagram includes:
(i) a first vertical axis for the first parameter,
(ii) a second vertical axis for the second parameter,
(iii) a third vertical axis for the third parameter, and
(iv) a line connecting measurements for a cell on each vertical axis included in the parallel coordinate plot.

14. The computer-implemented method of claim 11, wherein displaying the interactive control comprises:
generating a height for the interactive control based on a median fluorescence intensity value for a marker on the subset of the cells for the parameter associated with the interactive control.

15. The computer-implemented method of claim 11, wherein displaying the interactive control comprises:
generating a display color for the interactive control based at least in part on a color of an exciting laser or a fluorochrome for a marker associated with the parameter represented by the interactive control.

16. The computer-implemented method of claim 11, wherein displaying the interactive control comprises:
generating a display color for the interactive control based at least in part on a biological type associated with the parameter represented by the interactive control.

17. The computer-implemented method of claim 11, further comprising:
selectively displaying an analytic overlay, wherein the analytic overlay is displayed over at least a portion of the interactive control, the analytic overlay having a length representing a calculated metric for the parameter represented by the interactive control.

18. The computer-implemented method of claim 11, wherein the cell is taken from a sample, wherein the selection comprises a gate identifying a range of measurements defining the subset of the cells, and wherein the computer-implemented method further comprises:
receiving measurements, from a particle analyzer, for a second cell from the sample;
determining the second cell is included in the range of measurements; and wherein dynamically displaying the base object comprises adjusting at least one of the size or the shape of the base object based on the size of the subset of the cells; and wherein dynamically displaying respective interactive controls comprises adjusting at least one of a size or a shape of at least one interactive control further based at least in part on a second measurement for the second cell including in the measurements for the second cell.

19. An system for displaying a representation of multi-parametric cellular data for cells on a graphical user interface, the system comprising:
   a particle analyzer configured to detect, for each of the cells, measurements for respective markers of a plurality of markers; and
   graphics processing circuitry in communication with the particle analyzer, the graphics processing circuitry configured to:
   receive, from an input device, a first selection indicating a subset of the cells, and
   in response to receiving the first selection:
   dynamically display a base object, wherein at least one of a size or a shape of the base object is identified based at least in part on a size of the subset of the cells, and
   dynamically display respective interactive controls, wherein at least one of a size or a shape of an interactive control is identified based at least in part on a measurement for a cell for one of the plurality of markers, and wherein each interactive control is displayed at a respective point on the base object.

20. The system of claim 19, wherein the particle analyzer comprises at least one of: a flow cytometer or a single-cell analysis system.

21. The graphics control device of claim 1, wherein the shape of the base object is substantially circular and the size of the circular base object is identified based at least in part on a size of the subset of the cells.

22. The graphics control device of claim 21, wherein the shape of each interactive control is rectangular, a base of each interactive control shares a border with the perimeter of the substantially circular base object, each interactive control is positioned such that its height is radially oriented with respect to the substantially circular base object and the size of each interactive control is identified based at least in part on measurements for the subset of the cells.

* * * * *